(12) United States Patent
Link et al.

(10) Patent No.: US 12,004,955 B2
(45) Date of Patent: Jun. 11, 2024

(54) METHOD FOR TREATING A POLYMER WORKPIECE FOR USE IN A JOINT IMPLANT

(71) Applicant: WALDEMAR LINK GMBH & CO. KG, Hamburg (DE)

(72) Inventors: Helmut D. Link, Hamburg (DE); Carsten Schottler, Hamburg (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 29 days.

(21) Appl. No.: 17/661,975

(22) Filed: May 4, 2022

(65) Prior Publication Data
US 2022/0323226 A1    Oct. 13, 2022

Related U.S. Application Data

(62) Division of application No. 15/749,137, filed as application No. PCT/EP2016/067890 on Jul. 27, 2016, now Pat. No. 11,351,032.

(30) Foreign Application Priority Data

Jul. 31, 2015    (DE) .......................... 102015214668.5

(51) Int. Cl.
| | |
|---|---|
| *B29C 71/02* | (2006.01) |
| *A61F 2/30* | (2006.01) |
| *B29C 35/04* | (2006.01) |
| *B29C 37/02* | (2006.01) |
| *C08F 10/02* | (2006.01) |
| *C08L 23/06* | (2006.01) |

(52) U.S. Cl.
CPC ........ *A61F 2/30942* (2013.01); *A61F 2/3094* (2013.01); *B29C 35/045* (2013.01); *B29C 37/02* (2013.01); *B29C 71/02* (2013.01); *C08F 10/02* (2013.01); *C08L 23/06* (2013.01); *A61F 2002/30112* (2013.01); *C08F 2500/01* (2013.01)

(58) Field of Classification Search
CPC ....... A61F 2/30942; A61F 2002/30112; B29C 35/045; B29C 71/02; C08F 10/02; C08L 23/06
See application file for complete search history.

(56) References Cited

U.S. PATENT DOCUMENTS

| | | |
|---|---|---|
| 6,641,617 B1 | 11/2003 | Merrill et al. |
| 2009/0030524 A1 | 1/2009 | Schroeder et al. |
| 2012/0041446 A1 * | 2/2012 | Wong .................. A61F 2/30756 |
| | | 606/86 R |

FOREIGN PATENT DOCUMENTS

| | | |
|---|---|---|
| DE | 1752440 A1 | 2/1972 |
| DE | 3015335 A1 | 10/1981 |
| DE | 8609000 U1 | 8/1987 |
| DE | 19743076 C1 | 12/1998 |

(Continued)

*Primary Examiner* — Yung-Sheng M Tsui
(74) *Attorney, Agent, or Firm* — Chiesa Shahinian & Giantomasi PC

(57) ABSTRACT

The present invention provides a method for treating a polymer workpiece for use in a joint implant. It comprises the steps of placing the polymer workpiece in an explosion chamber, introducing a combustible gas mixture into the explosion chamber and igniting the combustible gas mixture. Igniting the gas mixture in the explosion chamber produces a temperature that lies above the melting point of a polymer of the polymer workpiece.

7 Claims, 4 Drawing Sheets

(56) References Cited

FOREIGN PATENT DOCUMENTS

| | | |
|---|---:|---|
| DE | 102012110819 A1 | 5/2014 |
| EP | 2898860 A1 | 7/2015 |
| RU | 2211008 C2 | 8/2003 |
| RU | 2328314 C2 | 7/2008 |
| RU | 116769 U1 | 6/2012 |
| WO | 84/04266 A1 | 11/1984 |
| WO | 2014/126908 A1 | 8/2014 |

\* cited by examiner

METHOD FOR TREATING A POLYMER WORKPIECE FOR USE IN A JOINT IMPLANT

This application is a Divisional of U.S. patent application Ser. No. 15/749,137, filed Jan. 31, 2018, which is a National Stage under 35 U.S.C. 371 of International Patent Application No. PCT/EP2016/067890, filed Jul. 27, 2016, which claims priority to German Patent Application No. 102015214668.5, filed Jul. 31, 2015, the disclosures of all are incorporated herein by reference in their entirety.

TECHNICAL FIELD

The present invention is in regard to a method for treating a polymer workpiece for use in a joint implant as well as components of a joint replacement produced with this method or instruments for implanting a joint replacement.

PRIOR ART

Polymer materials are used for orthopedic implants in a variety of ways. They often serve, for example in joint implants, so-called endoprostheses, as a material with which the artificial joint surface is formed. The anchorage of the polymer in the bone tissue is realized by means of an anchoring component which is produced, for example, of a steel alloy or a titanium alloy. When the metal component is anchored, adjacent bone tissue will grow into the prosthesis after implantation or it will be fixed in the bone tissue with the aid of bone cement. Consequently, the joint component of a polymer material is preferably carried out as an insert or attachment that is fixed to the anchoring component.

One polymer material that is often used for endoprostheses is polyethylene (PE), and in particular UHMWPE (Ultra High Molecular Weight Polyethylene). Compared to pure metal pairings, the surface thereof is characterized by a lower friction coefficient and high degree of adaptability. The latter leads to less wear, in particular during the run-in phase of the implant.

Despite this, wear still occurs also in joint components made of polyethylene, initially mainly due to manufacturing inaccuracies and later owing to daily loads. It has been known for some time in this regard that the polymer particles that detach during wear can cause osteolysis (lat.: bone disintegration) (Willert, H. G.; Buchhorn, G. H.; Hess, T.: "Die Bedeutung van Abrieb and Materia/ermudung bei der Prothesen/ockerung an der Hufte", Orthopade 18: 350-369, 1989). With osteolysis, polymer particles that detach from the polymer components reach the vicinity of the bone tissue, which can trigger a foreign body reaction. Endogenous cells then surround the polymer particles in the form of cell proliferation. Bone tissue may be displaced as a consequence of this, so that a loosening of the endoprosthesis may occur with increased probability. In the recent past, increased attention has in particular been paid the generation of such tissue proliferation, which is also effectively reflected in the description of this cancer-like proliferation as a pseudo tumor.

Based on the above, it is of interest to keep the number of polymer particles of an endoprosthesis as low as possible to prevent cell proliferation and the loosening of the endoprosthesis associated therewith.

SUMMARY OF THE INVENTION

In view of the problems described above, the present invention is based on the concept of improving the manufacturing quality, and therefore amongst other things also the fit accuracy of polymer components in order by this to reduce the number of polymer particles. The aim of this is to lower the probability of occurrence of osteolysis.

The present invention realizes this with the method defined in the independent claims. The associated dependent claims define preferred embodiments.

The method provided by the invention for treating a polymer workpiece for use with, and in particular in, a joint implant comprises placing the polymer workpiece in an explosion chamber, introducing a flammable gas mixture into the explosion chamber and igniting the flammable gas mixture, by which a temperature is produced by ignition of the gas mixture in the explosion chamber that lies above the melting point of a polymer of the polymer workpiece.

The explosion or sudden combustion caused by igniting the gas mixture results in the removal of any projecting polymer sections by burning or evaporation. Irregularities or deviations from the geometry to be produced that are due to manufacturing tolerances, such as e.g. projecting ridges or non-detached chips, are in particular removed by the method. Since no material residue or substances remain on the polymer workpiece after removal of irregularities due to manufacturing tolerances, the above-mentioned negative effects can no longer occur owing to this after implantation. The method therefore enables removal of these irregularities without reducing the biocompatibility of the polymer material.

Since burning takes place in an explosive way, this method is substantially faster compared to conventional methods, such as for example a manual post-treatment. Also a possibly complex geometry of the polymer workpiece does not play a role. Even sections on the surface of the polymer workpiece that are difficult to access can be reached with this method and stripped of irregularities. The removal of irregularities in accordance with the present invention prevents that these enter the body of the patient during implantation. The latter can in particular occur following manual deburring.

Unlike the removed material, the remaining material is not changed in a disadvantageous way. The geometry provided for the production of the polymer workpiece and the dimensions thereof remain substantially unchanged. The fit accuracy achieved in this way avoids relative movements between the anchoring component and the polymer workpiece and prevents the detachment of polymer particles.

The polymer workpiece preferably comprises just one polymer, but can also be formed from a polymer compound or a polymer mixture. The polymer workpiece preferably forms at least one section of the joint surface of the joint implant. At least one element for a connection with an anchoring component is preferably provided on the polymer workpiece, with which the polymer workpiece can be anchored to bone tissue.

In a further preferred embodiment, the polymer workpiece includes a thermoplastic, preferably polyethylene, and more preferably UHMWPE.

The method is in particular advantageously applicable with thermoplastics since these materials do not chemically change when exposed to heat generated during the explosion. In addition, not only are the above-mentioned irregularities removed, but deviations in the workpiece surface are also smoothed out.

One thermoplastic that is particularly suitable for the method is polyethylene. Polyethylene has proven itself as a material in artificial joints. This is in particular the case for UHMWPE for joint surfaces. It could also be established that treating the polymer workpiece does not cause any detectable changes in the material that could detrimentally affect biocompatibility or functionality, and therefore use inside the body, despite the high temperatures used.

With a further particularly preferred embodiment, the temperature lies within a range of 1500° C. to 2800° C., and preferably within a range of 2000° C. to 2500° C.

Said high temperature ranges for a polymer workpiece have been found to be particularly reliable for the removal of irregularities. Also the smoothing effect is achieved by these on the surface of the workpieces, where irregularities due to manufacturing tolerances are smoothed out without impacting the dimensions of the workpiece provided during production. In other words, owing to the method it is not necessary to add material during production, similar to casting components.

With a further preferred embodiment, the gas mixture to be exploded is introduced at a pressure of 1.5 to 2.1 bar, and preferably of 1.7 to 1.9 bar.

The gas mixture is introduced into the explosion chamber until said pressure ranges are reached. The gas quantity provided in this way will suffice to reach the temperatures by a one-off explosion-like combustion at which post-treatment of the polymer workpiece can take place. In other words, owing to these pressures the gas mixture needs to be introduced just once prior to the explosion. A further supply of gas is not necessary.

With a further embodiment, the polymer workpiece is pre-treated by means of machining.

The method is in particular of advantage for workpieces that have been pre-treated by means of machining since irregularities such as ridges and incompletely removed chips that normally have to be removed manually by hand at high cost are increasingly generated during machining treatment. Another compounding effect with joint components is that these often have a complex geometry that is firstly caused by the joint surface and secondly are a functional necessity, such as, for example, due to the connection thereof with an anchoring component. A further advantage of the method relates to the machining manufacturing process in that a smoothing of workpieces is no longer necessary at least in part since the method just as well removes irregularities generated more often during rough machining.

With a further particularly preferred embodiment of the method, the temperature produced by exploding the gas mixture of at least 1500° C., preferably of at least 2000° C., is maintained over a period of 1 ms to 10 ms, preferably 1 ms to 5 ms, and more preferably 1 ms to 2 ms.

These combinations of minimum temperature and the time period over which the temperature is maintained ensure the removal of the irregularities remaining owing to the molding. The shorter periods already suffice here to at least burn or evaporate freely projecting irregularities. The longer the period, the more pronounced the additional smoothing effect is.

With a particularly preferred embodiment of the invention, the gas mixture comprises oxygen and methane.

This gas mixture produces the temperatures required for removing possible irregularities on the workpiece in a reliable and controlled way. It also ensures clean combustion, so that no residue remains on the workpiece that would have to be removed in some other way to retain the biocompatibility of the polymer workpiece. The gas mixture is preferably pre-mixed to ensure a homogeneous distribution of the components of the gas mixture.

The present invention also provides a joint implant with a polymer component, with the polymer component having been produced with the method described above and the polymer component forming part of a hip-joint replacement, a knee-joint replacement, in particular a tibia plateau, a shoulder-joint replacement, an ankle-joint replacement, an elbow-joint replacement, a finger-joint replacement or a mega prosthesis.

The present invention also provides an instrument for implanting a joint replacement that comprises a component made of a sterilized thermoplastic produced with the method described above.

In summary, the method carries out treatment or post-treatment of the workpiece in an extremely efficient way, namely not only with regard to manufacturing costs. Owing to the high degree of reliability when removing irregularities on the workpiece surface, a detachment of these irregularities following implantation is also successfully prevented, and with it the negative consequences of polymer particles embedded in or on tissue described above.

BRIEF DESCRIPTION OF THE FIGURES

The following figures illustrate the following detailed explanation of preferred embodiments of the present invention, wherein.

DETAILED DESCRIPTION OF PREFERRED EMBODIMENTS

Figure 1:
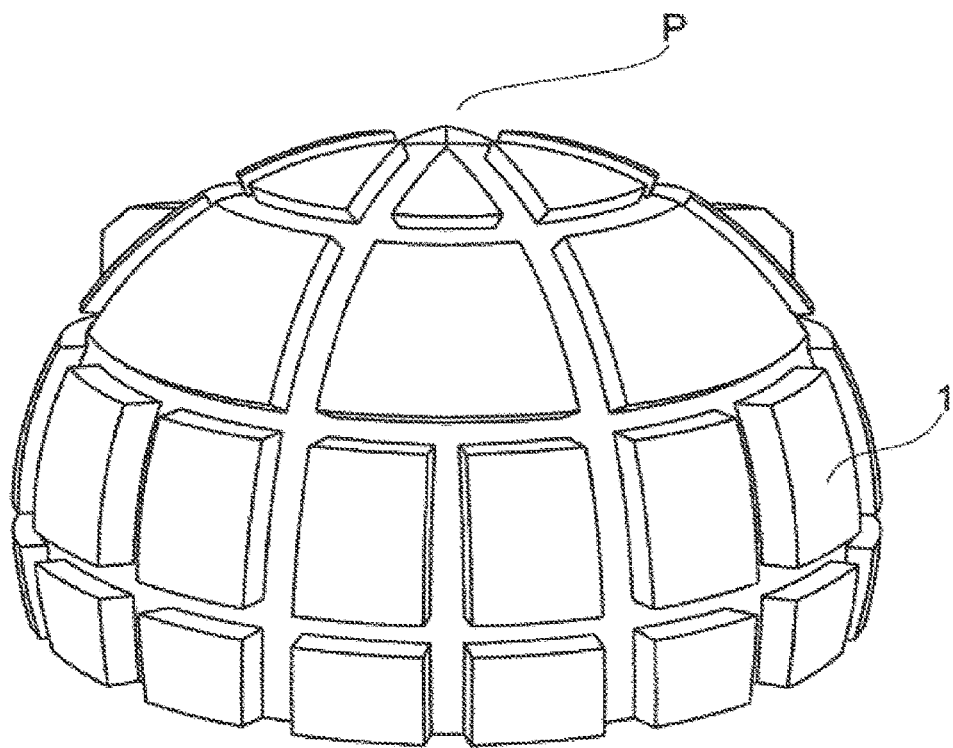
FIG. 1 shows a polymer workpiece for use in a joint implant.

FIG. 1 shows a polymer workpiece 1 provided for use in a joint implant. The polymer workpiece 1 shown is a hip joint insert of UHMWPE, which can be inserted into a metal hip socket which is in turn provided for implantation into the acetabulum of a patient. To put it differently, the joint insert illustrated in FIG. 1 is anchored in the bone tissue using a not-shown hip socket of a polymer material.

The complexity of the external geometry that a joint insert can have also becomes clear from FIG. 1. The hip joint insert shown in FIG. 1 is just one example of the many varied application possibilities of the method for joint implantation. It can be used for the most varied joints, such as for example hip sockets or inserts, tibia plateaus of knee joints, knee-joint inserts, shoulder-prosthesis components, ankle-joint components, elbow-joint components, megaprosthesis components and can be used for instruments made from sterilizable thermoplastics.

Owing to the precise and reliable removal of irregularities that is substantially carried out without material removal from the target geometry, the method can also be used particularly advantageously for smaller joint components, such as, for example, finger joints like the thumb-saddle joint. Particularly with these comparatively small joints, and thus smaller polymer workpieces 1, deburring by hand leads to a relatively strong change in the workpiece geometry.

Irregularities as part of this invention are understood as projections created owing to the manufacture of the polymer workpiece 1. These include ridges G and chips S generally generated by cutting processes, but also polymer particles 22 pressed into or against the workpiece surface (compare FIG. Sa). It is also possible to reduce irregularities on the surface introduced by cutting processes.

Workpieces 1 to be used in a joint replacement are preferably cast by means of injection molding. Consequently, a thermoplastic that also has the advantages already listed above in connection with the method is preferred as a polymer material. In a normal case, machining treatment methods will also be used, i.e. whether a geometry is to be drilled or milled from solid material or if projections remaining after casting, such as for example mold seams, are to be removed.

Figure 7:
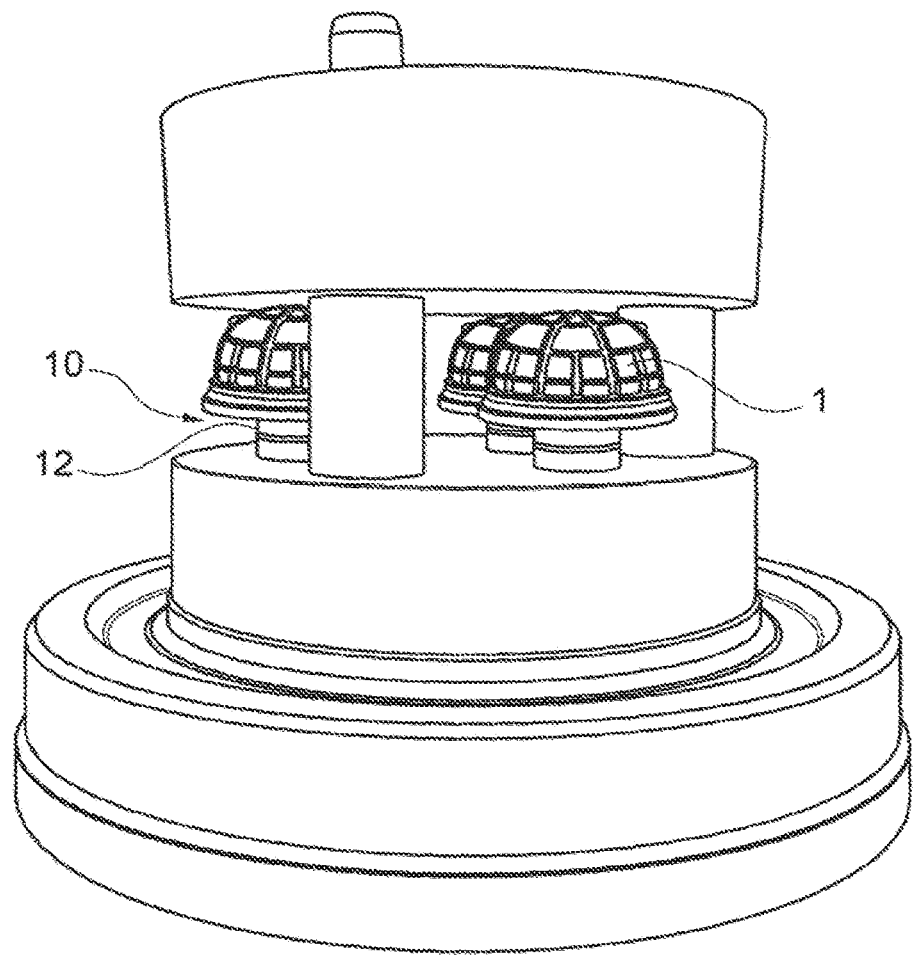
FIG. 7 shows workpieces in a holder prior to carrying out explosion deburring.

A polymer workpiece 1 pre-fabricated in this way and illustrated as an example in FIG. 1 is thereafter fixed on a holder 12 in an explosion chamber or an explosion chamber insert 10 for applying the method (see FIG. 7). With the explosion chamber insert 10 illustrated in FIG. 7, three polymer workpieces 1 can be treated simultaneously. The explosion chamber is formed by inserting the explosion chamber insert 10 into a corresponding opening. The free volume of the explosion chamber to be filled with the gas mixture that is determined by this is approximately 10 times to 30 times, preferably 15 times to 25 times, the volume of the polymer workpieces 1.

Following placement in the explosion chamber, this is closed and the flammable, preferably pre-mixed gas mixture such as for example that mentioned above, is introduced.

The gas mixture is thereafter ignited so that an explosion-like combustion similar to that of an internal combustion engine takes place. The combustion process is controlled here in particular by adding a corresponding quantity of the gas mixture in such a way that temperatures of 1500° C. to 2800° C., and preferably of 2000° C. to 2500° C., are reached in the explosion chamber.

The period over which the temperatures of said temperature range are reached is selected in such a way that existing irregularities are removed by combustion or evaporation. The period required for this normally lies within the millisecond range and in particular within a range of 1 ms to 10 ms, preferably 1 ms to 5 ms, and more preferably 1 to 2 ms. A very short period such as, for example, the latter will suffice for substantially removing existing irregularities.

Said longer periods will also lead to an increased smoothing effect on the surface of the workpiece 1.

The overpressure generated by the combustion is vented from the explosion chamber in a controlled way. The entire explosion deburring process only takes approximately 1 minute. In other words, approximately 1 minute will elapse from one ignition to the next ignition, with several workpieces 1 being able to be treated simultaneously with each ignition, as illustrated in FIG. 7.

The advantages achieved with the method will be illustrated below with reference to FIGS. 2 to 6 by way of an example of treating a polymer workpiece 1 as shown in FIG. 1.

Figure 2:
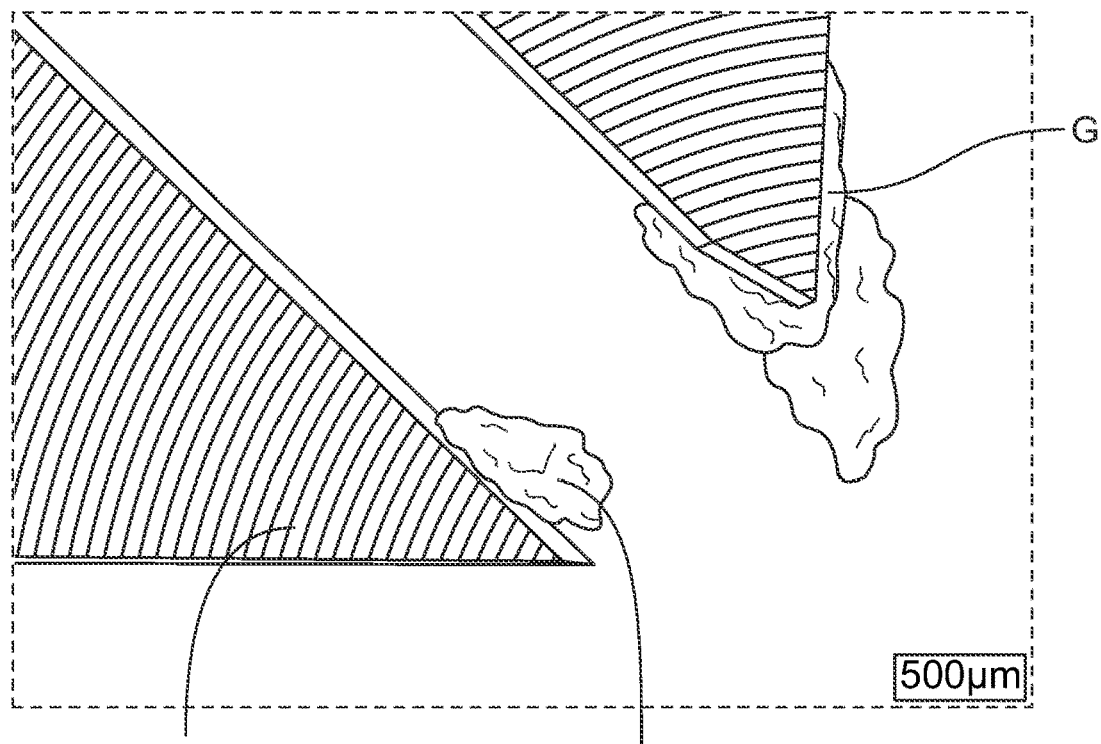
FIG. 2 shows a section of the polymer workpiece from FIG. 1 following machining treatment.

FIG. 2 shows the pole section P from FIG. 1 in an enlarged presentation following machining treatment, with which the complex geometry illustrated in FIG. 1 is produced. In FIG. 2, the resulting ridges G and chips S can be seen which were generated by the machining treatment and which have not detached themselves from the workpiece 1.

One treatment method normally used for such workpieces 1 is manual deburring, which is mostly carried out by hand. The result of such a deburring by hand is illustrated in FIG. 3, which shows a section that equals the section shown in FIG. 2 at the same enlargement.

Deburring is also a machining process. In other words, a deburring by hand allows for the possibility that chips and ridges will not only remain, but will be newly created. One of these reasons has led to chip S still being present in FIG. 3.

Figure 3:
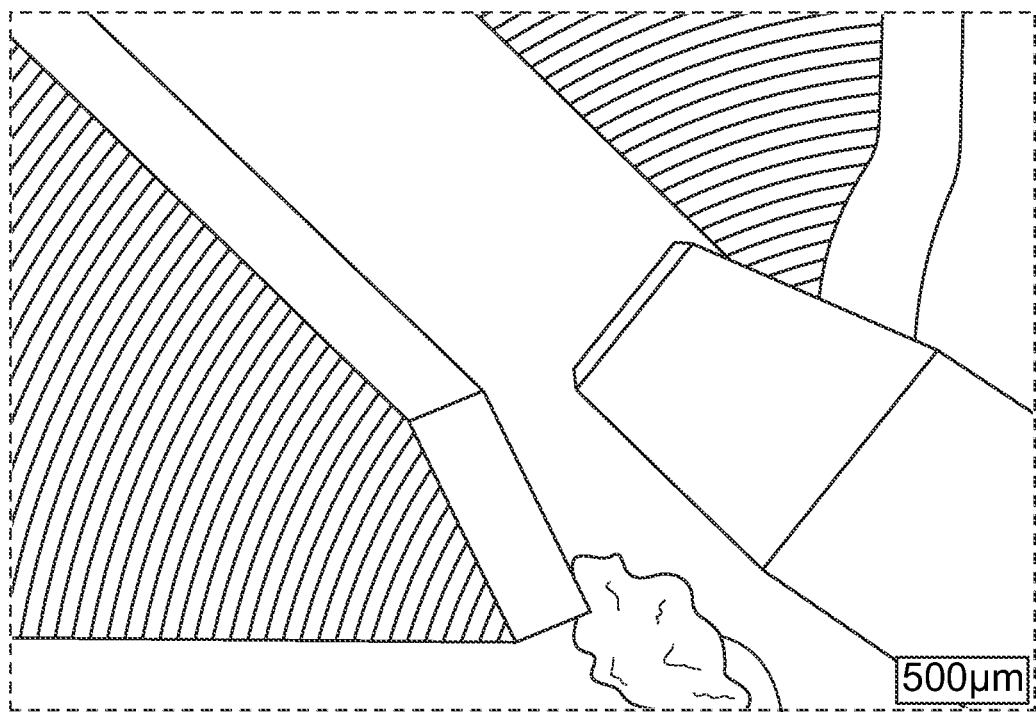
FIG. 3 shows a section comparable to the section from FIG. 2 following manual deburring by hand.

The change in workpiece geometry following manual deburring is also particularly evident in FIG. 3. The triangular or cake-wedge shaped tips on the pole side P of the polymer workpiece 1 of FIG. 1 are here repositioned and blunted owing to manual post-processing. This localized size reduction in the geometry increases the probability that a relative movement is possible between the polymer workpiece 1 shown and the associated anchoring component, i.e. in this case a hip socket. Such movements within the micrometer range can also detach polymer particles. This once again favors the occurrence of osteolysis in the area of bone tissue that lies in the vicinity of the artificial joint replacement, i.e. the anchoring component. This is true in particular for the interface area between the polymer workpiece 1 and the anchoring component connected therewith that faces the tissue.

Figure 4:
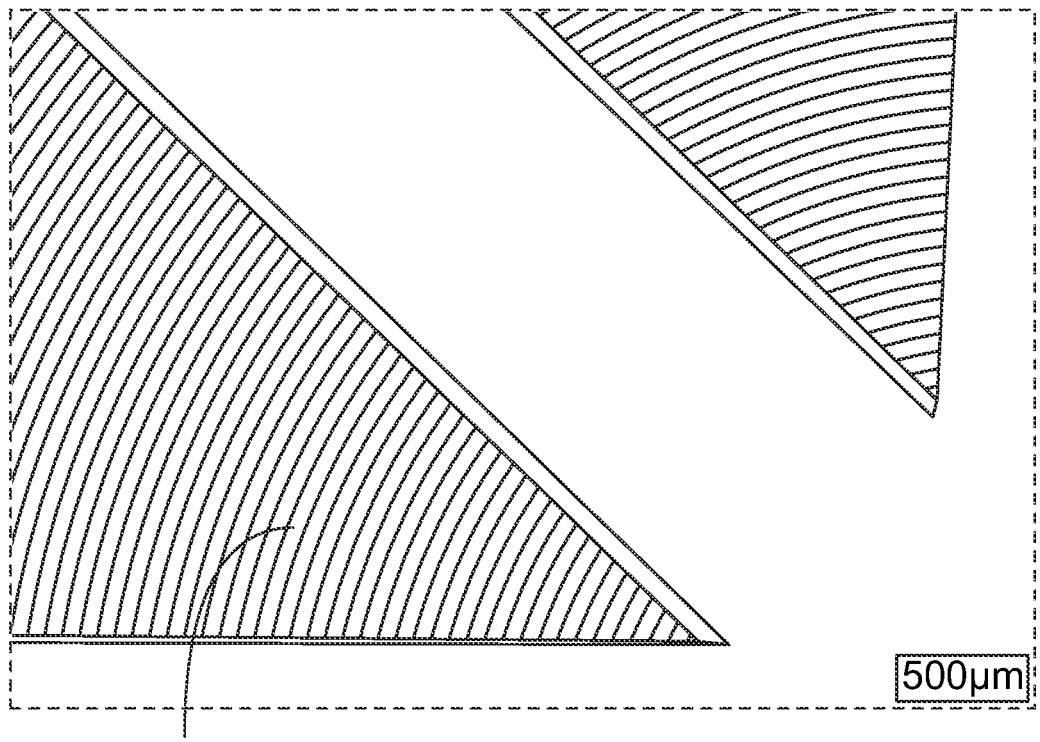
FIG. 4 shows a section comparable to the section from FIG. 2 following treatment of the workpiece with the method according to the invention.
Figure 5:
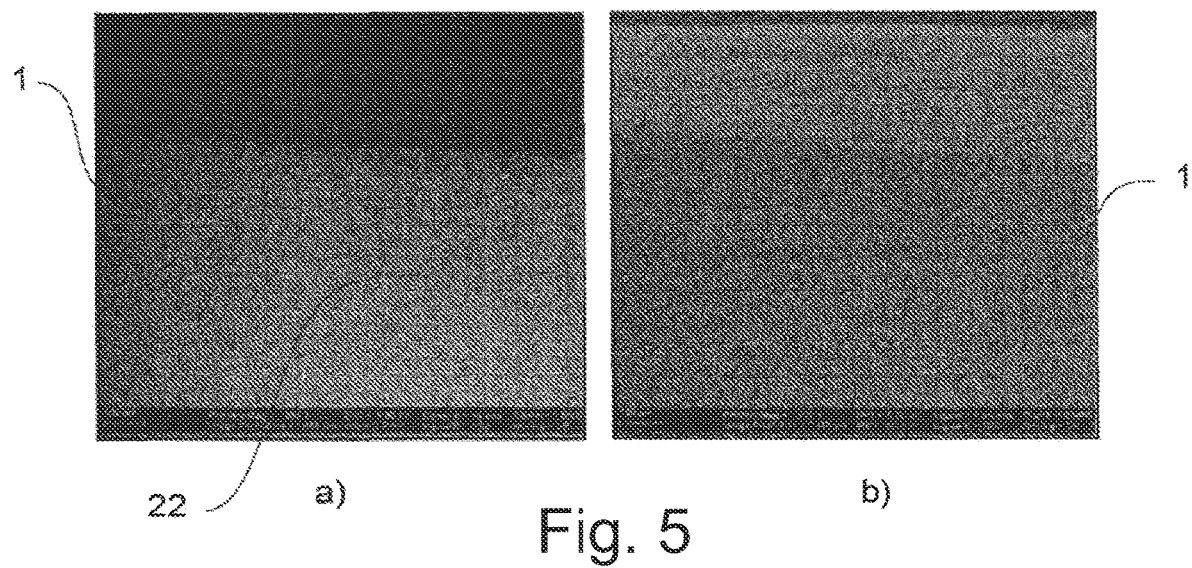
FIG. 5 shows an image taken with a scanning electron microscope, with FIG. 5a) showing the surface of the workpiece in an edge area following manual deburring by hand and FIG. 5b) showing the surface of the workpiece in a comparable edge area after using the method according to the invention.
Figure 6:
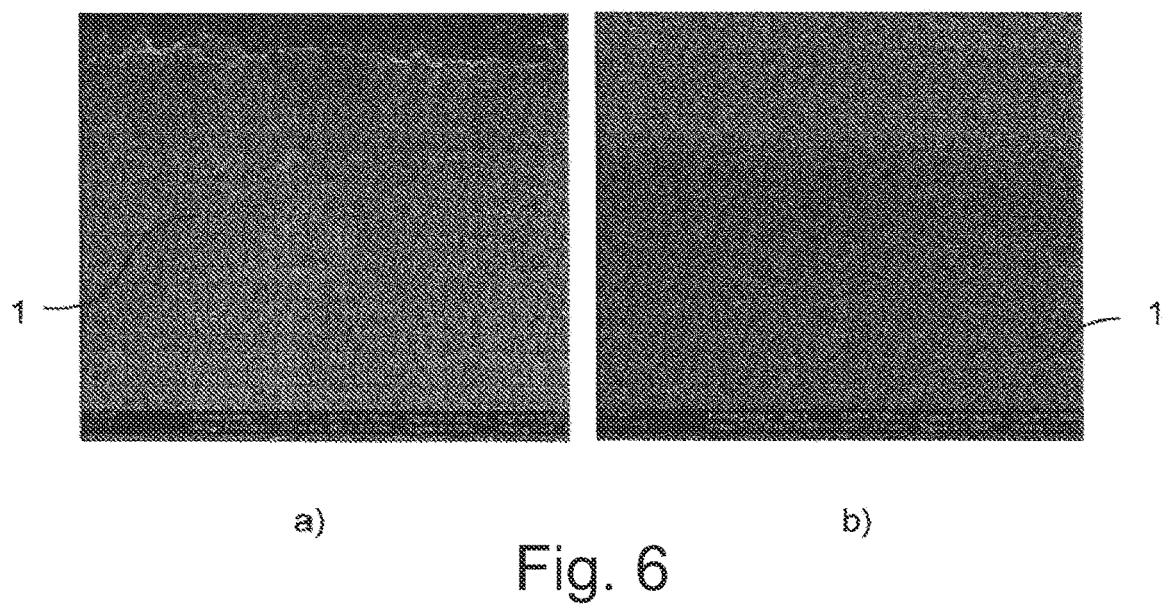
FIG. 6 shows an image taken with a scanning electron microscope in a higher resolution compared to FIG. 5, with FIG. 6a) illustrating the surface of the workpiece in an edge area following manual deburring by hand and FIG. 6b) illustrating the surface of the workpiece in a comparable edge area after using the method according to the invention.

Unlike FIG. 3, the method according to the invention was used as a treatment method for the section of a polymer workpiece 1 shown in FIG. 4. It can be clearly seen from this section, which in turn corresponds to the section of the untreated polymer workpiece 1 shown in FIG. 2, that the workpiece geometry remaining after applying the method according to the invention comes much closer to the ideal geometry, namely that envisaged by the construction. Consequently, a higher fit accuracy can be realized with sections for a connection between the polymer workpiece 1 and the anchoring component, and thus the micro-movements mentioned above can be prevented.

Figures Sand 6 show an enlarged section of an edge area of the polymer workpiece 1 from FIG. 1. FIGS. 6a and 6b show a section like that of FIGS. Sa and Sb, although in a view that has been enlarged yet again. FIGS. Sa and 6a illustrate the result achieved with deburring by hand, whilst FIGS. Sb and 6b show the treatment result achieved with the method according to the invention.

Manual deburring was carried out on the workpiece 1 shown in FIGS. Sa and 6a, where only the macroscopic irregularities recognizable in FIG. 2 could, however, be removed due to the deburring process and the properties of the polymer material. It does become clear from the scanning electron microscopic images in FIGS. Sa and 6a, however, that the remaining ridges or chips cannot be removed completely during deburring. The deburring, which is a cutting process in itself, also creates a new, if somewhat smaller ridge. This is illustrated in the upper area of FIG. Sa, and is once again illustrated more easily recognizable in an enlarged form in the upper area of FIG. 6a.

It is also clear in FIG. 5a that on the surface polymer particles 22 are pressed into the workpiece surface due to the deburring process. These pose the risk that they may loosen when subjected to mechanical loads following implantation and could cause the disadvantages mentioned above.

The sections of a polymer workpiece 1 shown in FIGS. 5b and 6b, which show a workpiece surface produced with the method, are, however, of a much more even appearance. No irregularities comparable to those in FIGS. 5a and 6a can be found on the workpiece surface in FIGS. 5b and 6b. Instead the surface shown has an almost smooth appearance created with the method by the brief high temperature increase in the explosion chamber. This also prevents a subsequent breakout or detachment of polymer particles 22 from the polymer workpiece 1 of the implanted artificial joint.

A breakout of polymer particles 22 is in particular prevented especially in the edge area of a joint surface. It is exactly in this area in which the polymer workpiece 1 is subjected to great loads due to spatial contact with its joint partner in its implanted condition that the risk of a breakout of polymer particles is particularly high, but can be lowered substantially by using the present method.

Overall not only are cost advantages realized due to the omission of complex deburring by hand and a clear acceleration of processing, but qualitative advantages are also achieved by the increased accuracy and comprehensive treatment of the workpiece surface.

REFERENCE NUMBERS

1 Polymer workpiece
10 Explosion chamber insert
12 Holder for workpiece
22 Polymer particle
P Pole side
G Ridge
S Chip

The invention claimed is:

1. A joint implant having a polymer component with a smoothened surface, wherein the polymer component is produced by:
   placing a polymer workpiece in an explosion chamber;
   closing the explosion chamber;
   introducing a flammable gas mixture into the explosion chamber; and
   igniting the flammable gas mixture, wherein a temperature that lies above the melting point of the polymer and in a range of 1500° C. to 2800° C. is produced in the explosion chamber by igniting the gas mixture for smoothening the surface of the polymer component, and wherein igniting the flammable gas mixture in the explosion chamber also treats the polymer component by deburring.

2. The joint implant of claim 1, wherein the joint implant is selected from the group consisting of a hip joint replacement, a knee joint replacement, a tibia plateau, a shoulder-joint replacement, an ankle-joint replacement, an elbow-joint replacement, a finger-joint replacement, and a megaprosthesis.

3. The joint implant of claim 1, in which the polymer workpiece comprises a thermoplastic.

4. The joint implant of claim 1, wherein the polymer workpiece is introduced to a gas mixture to be exploded at a pressure of 1.5 to 2.1 bar.

5. The joint implant of claim 1, wherein the polymer workpiece is pre-treated by means of deburring by hand, deburring by milling, deburring by turning, and combinations thereof.

6. The joint implant of claim 1, wherein the polymer workpiece is exposed to a temperature produced by exploding the gas mixture in a range of 1500° C. to 2800° C. and is maintained over a period of 1 ms to 10 ms.

7. The joint implant of claim 1, wherein the gas mixture to which the polymer workpiece is exposed comprises oxygen and methane.

* * * * *